US008992232B2

(12) United States Patent
Berry et al.

(10) Patent No.: US 8,992,232 B2
(45) Date of Patent: Mar. 31, 2015

(54) INTERACTIVE AND EDUCATIONAL VISION INTERFACES

(71) Applicant: Orca Health, Inc., Sandy, UT (US)

(72) Inventors: Matthew M. Berry, Highland, UT (US); Jacob S. Lybbert, Provo, UT (US); Robert M. Berry, Highland, UT (US); Wesley D. Chapman, Draper, UT (US); Christopher T. Owens, Provo, UT (US)

(73) Assignee: Orca Health, Inc., Sandy, UT (US)

( * ) Notice: Subject to any disclaimer, the term of this patent is extended or adjusted under 35 U.S.C. 154(b) by 0 days.

(21) Appl. No.: 13/838,865

(22) Filed: Mar. 15, 2013

(65) Prior Publication Data

US 2013/0211284 A1    Aug. 15, 2013

Related U.S. Application Data

(63) Continuation-in-part of application No. 13/237,530, filed on Sep. 20, 2011.

(51) Int. Cl.
*G09B 23/28* (2006.01)
*A61B 3/02* (2006.01)
*G09B 5/02* (2006.01)

(52) U.S. Cl.
CPC . *A61B 3/02* (2013.01); *G09B 23/28* (2013.01); *G09B 5/02* (2013.01)
USPC ............... 434/267; 351/237; 715/823; 705/2; 600/300

(58) Field of Classification Search
USPC ........................................................ 434/267
See application file for complete search history.

(56) References Cited

U.S. PATENT DOCUMENTS

| | | | |
|---|---|---|---|
| 5,748,907 A | 5/1998 | Crane | |
| 5,766,016 A | 6/1998 | Sinclair et al. | |
| 5,924,074 A | 7/1999 | Evans | |
| 6,383,135 B1 * | 5/2002 | Chikovani et al. ............ | 600/300 |
| 7,107,547 B2 * | 9/2006 | Cule et al. ..................... | 715/810 |
| 7,962,348 B2 | 6/2011 | Dew et al. | |
| 2002/0082865 A1 * | 6/2002 | Bianco et al. .................... | 705/2 |
| 2003/0208324 A1 | 11/2003 | Bellwood et al. | |
| 2005/0104896 A1 | 5/2005 | Kerr | |
| 2007/0236514 A1 | 10/2007 | Agusanto et al. | |
| 2007/0242069 A1 | 10/2007 | Matsue | |
| 2008/0027917 A1 | 1/2008 | Mukherjee | |
| 2008/0136838 A1 | 6/2008 | Goede et al. | |
| 2008/0177602 A1 | 7/2008 | Sopher et al. | |
| 2008/0242953 A1 | 10/2008 | Dew et al. | |
| 2010/0070297 A1 | 3/2010 | Kharraz Tavakol et al. | |
| 2010/0070300 A1 * | 3/2010 | Anderson et al. ................ | 705/2 |
| 2010/0257214 A1 | 10/2010 | Bessette | |
| 2010/0287001 A1 | 11/2010 | Pearce et al. | |

(Continued)

OTHER PUBLICATIONS

VueCare Media, Vue Simulator, Demo video accessed at: http://www.vuecaremedia.com/vuesim_demo.html, copyright 2010.*

(Continued)

*Primary Examiner* — Xuan Thai
*Assistant Examiner* — James Hull
(74) *Attorney, Agent, or Firm* — Workman Nydegger

(57) ABSTRACT

User interfaces facilitate user interaction with virtual representations of anatomical structures that are displayed on computing systems. The user interfaces demonstrably reflect relative impacts on the anatomical structures based on corresponding conditions and treatments.

14 Claims, 15 Drawing Sheets

(56) References Cited

U.S. PATENT DOCUMENTS

| | | |
|---|---|---|
| 2011/0145693 A1 | 6/2011 | Mutic |
| 2011/0170752 A1 | 7/2011 | Martin et al. |
| 2011/0264503 A1 | 10/2011 | Lenahan et al. |
| 2012/0159391 A1 | 6/2012 | Berry et al. |
| 2012/0206694 A1* | 8/2012 | Raskar et al. ............... 351/237 |
| 2012/0280988 A1 | 11/2012 | Lampotang et al. |
| 2013/0315452 A1 | 11/2013 | Berry et al. |
| 2014/0022283 A1 | 1/2014 | Chan et al. |
| 2014/0122096 A1 | 5/2014 | Berry et al. |
| 2014/0204118 A1 | 7/2014 | Berry et al. |
| 2014/0215370 A1 | 7/2014 | Berry |

OTHER PUBLICATIONS

VueCare Media, Vue Simulator, About page accessed at: http://web.archive.org/web/20110207031345/http://vuecaremedia.com/vuesim.html, captured Feb. 7, 2011.*

VueCare Media: The Eye Channel Network press release accessed at http://vuecaremedia.com/Final%20Press%20Release%202011-1-10.pdf (created Dec. 23, 2010).*

VueCare Media, Vue Simulator, Demo video accessed at: http://www.vuecaremedia.com/vuesim_demo.html.copyright 2010.

U.S. Appl. No. 13/237,530, Feb. 1, 2013, Office Action.

U.S. Appl. No. 13/237,530, Apr. 19, 2013, Office Action.

U.S. Appl. No. 14/477,540, filed Sep. 4, 2014, Berry et al.

U.S. Appl. No. 14/251,400, filed Apr. 11, 2014, Mainwaring et al.

U.S. Appl. No. 62/045,968, filed Sep. 4, 2014, Mainwaring et al.

Biggs, John, Up Close With Biodigital's 3D Human Simulator [TCTV]TCTechCrunch, Apr. 25, 20120, http://techcrunch.com/2012/04/25/up-close-with-biodigitals-3d-human-simulator-tctv/.

Pivi & Co, FatBooth, http://itues.apple.com/us/app/fatbooth/id372268904?mt=8, Available at least as early as Dec. 19, 2012, Version 3.4.

Welcome to the AR Lungs Website, http://www.arlungs.com/, Available at least as early as Jan. 7, 2013.

Mirracle, http://mirracle.de/, First Prototype of Magic Mirror, Jan. 3, 2011.

U.S. Appl. No. 13/093,272, Dec. 4, 2013, Office Action.

U.S. Appl. No. 13/093,272, May 16, 2014, Notice of Allowance.

U.S. Appl. No. 13/237,530, Oct. 1, 2013, Office Action.

U.S. Appl. No. 13/237,530, Mar. 20, 2014, Office Action.

U.S. Appl. No. 13/477,794, May 20, 2014, Office Action.

U.S. Appl. No. 13/477,794, Aug. 29, 2014, Notice of Allowance.

U.S. Appl. No. 13/663,820, Jun. 6, 2014, Office Action.

U.S. Appl. No. 13/663,820, Oct. 2, 2014, Office Action.

U.S. Appl. No. 13/747,595, Oct. 8, 2014, Office Action.

* cited by examiner

INTERACTIVE AND EDUCATIONAL VISION INTERFACES

CROSS-REFERENCE TO RELATED APPLICATIONS

This application is a continuation-in-part of U.S. patent application Ser. No. 13/237,530 filed on Sep. 20, 2011 and entitled "INTERACTIVE AND EDUCATIONAL VISION INTERFACES," which application is expressly incorporated herein by reference in its entirety.

BACKGROUND OF THE INVENTION

1. The Field of the Invention

The present invention is generally related to user interfaces and, even more particularly, to medically-related interactive user interfaces that are rendered on display devices, which facilitate user interaction with virtual representations of anatomical structures and, some of which, demonstrably reflect the impact of various conditions and treatments on the anatomical structures.

2. The Relevant Technology

Specialized computing devices are now available to benefit almost every aspect of human life. Many of these computing devices include user interfaces through which a consumer is able to provide and receive relevant information. In some instances, for example, a consumer can provide touch input through a user interface to effectively manipulate data that is rendered by software applications on the display screen.

While computers have been used in the medical industry for quite some time to facilitate user interaction with representations of anatomical structures, a need still exists for improved medical applications that are capable of providing relevant information to consumers on-demand and in a user-friendly and intuitive manner. In particular, the medical industry has a need for new and improved user interfaces that are capable of utilizing the increased computational capabilities of current computing devices to further facilitate user interaction with representations of anatomical structures and to demonstrably reflect the impact of various conditions and treatments on anatomical structures through these representations.

BRIEF SUMMARY OF THE INVENTION

The present invention extends to methods, systems, and computer program products for utilizing user interfaces to facilitate user interaction with representations of anatomical structures and to demonstrably reflect the impact of various conditions and treatments on anatomical structures through these representations.

User interfaces are utilized to display representations of anatomical structures, such as an eye structure. Interface elements are also displayed and available for user selection to facilitate an interactive exploration and/or modification of the displayed anatomical structure(s).

In some instances, a modified anatomical structure is displayed to reflect the impact of one or more selected conditions. The modified anatomical structure is also displayed simultaneously with interactive treatment elements that correspond to possible treatments for the condition(s). Modifications to the anatomical structure can also reflect the impact of one or more selected interactive treatment elements(s) applied to the relevant condition(s).

In some embodiments, the modified anatomical structure is displayed with a dynamic perception image that reflects a relative perception that a person with the condition might see. This dynamic perception image is then dynamically altered when a severity of the condition, or another condition variable, is modified through user input. Changes in the severity of the condition can also be reflected by making additional modifications to the displayed anatomical structure to show the impact changes in the condition may have on the anatomical structure.

Interface elements are also provided to enable a user to identify and/or contact specialists who are trained in the diagnosis of related conditions and/or the application of treatments for the corresponding anatomical structures.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
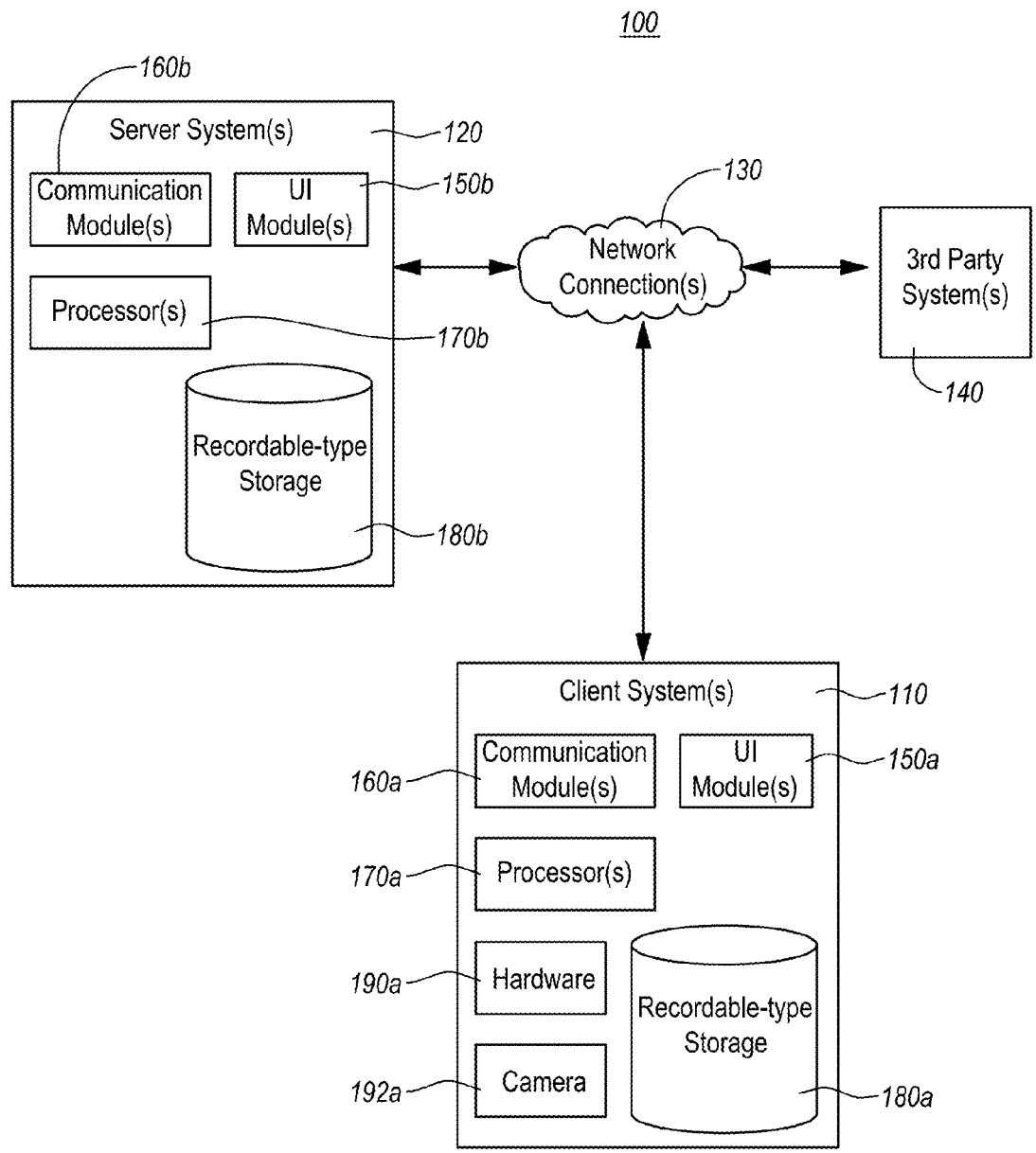
FIG. 1 illustrates one example of a computing environment that can utilize the user interfaces of the invention.

User interfaces are utilized in the methods, systems, and computer program products of the present invention for facilitating user interaction with anatomical structures and to demonstrably reflect the impact of various conditions and treatments on those anatomical structures. User interfaces are also used to facilitate contact and communication with relevant medical professionals.

In some embodiments, mobile devices are utilized to access the inventive user interfaces. In other embodiments, desktop devices, servers, kiosks, mobile phones, gaming systems and/or other devices are used.

Preferably, although not necessarily, the consumer devices have touch screens, such as on a tablet computing device, that can be used to receive user input and to display relevant output. In other embodiments, keyboards, rollers, touch pads, sticks, mice, microphones and/or other input devices are used to receive input. Speakers, printers and display screens, which are not touch sensitive, can also be used to render corresponding output.

In one embodiment, a user interface is utilized to display an anatomical structure, such as an eye structure, along with user interface elements that can be selected to facilitate a manipulation and interactive exploration of the displayed anatomical structure.

The user interfaces of the invention are utilized to display the anatomical structure after it has been modified with a selected condition and/or treatment. Dynamic perception images can also be displayed to reflect the impact of a selected condition and/or treatment and at varying stages of the condition. Interface elements are also provided to enable a user to initiate contact with specialists trained in treatments associated with the anatomical structure and corresponding conditions.

In some embodiments, mobile consumer devices have touch screens that are utilized to receive user input and to display output associated with the user interfaces of the invention. In other embodiments, keyboards, rollers, touch pads, sticks, mice, microphones and other input devices are used to receive input at the consumer devices. Speakers and display screens, which are not touch sensitive, can also be used to render corresponding output.

Computing Environment(s)

Embodiments of the present invention may comprise or utilize special purpose or general-purpose computing devices that include computer hardware, such as, for example, one or more processors and system memory, as discussed in greater detail below. Embodiments within the scope of the present invention also include physical and other computer-readable and recordable type media for storing computer-executable instructions and/or data structures. Such computer-readable recordable media can be any available media that can be accessed by a general purpose or special purpose computer system. Computer-readable media that store computer-executable instructions according to the invention are recordable-type storage media or other physical computer storage media (devices) that are distinguished from merely transitory carrier waves.

Computer-readable media that carry computer-executable instructions are transmission media. Thus, by way of example, and not limitation, embodiments of the invention can comprise at least two distinctly different kinds of computer-readable media: computer storage media (devices) and transmission media.

Computer storage media (devices) includes RAM, ROM, EEPROM, CD-ROM, DVD-ROM, HD-DVD, BLU-RAY or other optical disk storage, magnetic disk storage or other magnetic storage devices, or any other medium which can be used to store desired program code means in the form of computer-executable instructions or data structures and which can be accessed by a general purpose or special purpose computer and which are recorded on one or more recordable type medium (device).

A "network" is defined as one or more data links or communication channels that enable the transport of electronic data between computer systems and/or modules and/or other electronic devices. When information is transferred or provided over a network or another communications connection or channel (either hardwired, wireless, or a combination of hardwired or wireless) to a computer, the computer properly views the connection as a transmission medium. Transmissions media can include a network and/or data links which can be used to carry or desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that computer storage media (devices) can be included in computer system components that also (or even primarily) utilize transmission media.

Computer-executable instructions comprise, for example, instructions and data which, when executed at one or more processor, cause one or more general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described herein. Rather, the described features and acts are disclosed as example forms of implementing the claims.

Those skilled in the art will appreciate that the invention may be practiced in network computing environments with many types of computer system configurations, including, personal computers, desktop computers, laptop/notebook computers, message processors, hand-held devices, multi-processor systems, microprocessor-based or programmable consumer electronics, network PCs, minicomputers, mainframe computers, tablets, mobile telephones, PDAs, pagers, routers, switches, and the like. The invention may also be practiced in distributed and cloud system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

FIG. 1 illustrates an exemplary computing environment 100 that can be used to present the user interfaces of the invention, to facilitate user interaction with anatomical structures rendered on the user interfaces, and to demonstrably reflect the impact of various conditions and treatments on those anatomical structures.

As shown, the computing environment 100 includes one or more client systems 110 in communication with one or more server systems 120 through one or more network connections 130. The network connections 130 can include any combination of Local Area Network ("LAN") connections, Wide Area Network ("WAN") connections, including the Internet and one or more proxy servers.

The client and server systems 110, 120 are also shown to be in communication with one or more third party systems 140 through the network connections 130.

It will also be appreciated that each of the illustrated systems can comprise standalone systems (as generally shown) or, alternatively, distributed systems.

As illustrated, the client and server systems 110, 120 are each configured with a plurality of user interface modules 150a, 150b and communication modules 160a, 160b that each comprise computer-executable instructions and data structures for implementing aspects of the invention.

The communication modules 160a, 160b include computer-executable instructions that, when executed by one or more processors 170a, 170b, are operable to facilitate wireless and/or wired communications through the network connections 130. Any data can be included in the communications, including image data, sound data, and textual data. The communication modules are also configured to encrypt and decrypt data and to perform authentication of user and system credentials.

The interface modules 150a, 150b include computer-executable instructions that, when executed by the one or more processors 170a, 170b, are operable to generate and/or present user interfaces such as the interfaces described herein.

The client and server systems 110, 120 also include recordable-type storage 180a, 180b, such as, but not limited to system memory. The storage 180a, 180b can store any type and quantity of different data, including the interfaces described herein, as well as the various modules described above. It will also be appreciated that the storage 180a, 180b can be distributed among a plurality of different devices or systems, including the third party systems 140, and does not necessarily need to be constrained to a single physical device. In some embodiments, however, the storage 180a and/or 180b are constrained to a single device.

In some embodiments, the client system 110 comprises a wireless cell phone, a tablet computer, a notebook computer, a PDA, and/or any other type of smart device having a display screen and/or speakers that are included within the hardware 190a of the mobile device and that are capable of rendering image data, audio data, and/or textual data to a user via the interface modules 150a and/or 150b, for example. In some embodiments, the hardware 190a of the client system 110 also includes a touch screen capable of receiving touch input at the display screen of the client system 110.

In some embodiments, the hardware 190a includes a camera 192a or other image capturing hardware which is selectably operable in response to user input. The user input can be entered through any combination of hardware and software objects. For instance, user input can be entered when a user selects an icon that is rendered on a display screen, such as, for example, in response to a user touching a camera control icon 733 (shown in FIG. 7A), or another icon or control button associated with the camera or client system 110.

It will be appreciated that display and audio hardware 190a, including camera 192a, of the client system 110 and corresponding hardware on third party systems 140 can be particularly useful during implementation of various embodiments described herein to enable medical professionals and users to remotely interface via video conferencing or teleconferencing.

Each of the systems shown, including the server system 120 and third party systems 140 include any hardware, storage, and software components useful for implementing the functionality of the invention, and can include, therefore, any of the hardware and software components described throughout this paper. For instance, it will be appreciated that the server system also includes various hardware, although not shown, similar to or the same as the hardware 190a of the client system 110.

Figure 2:
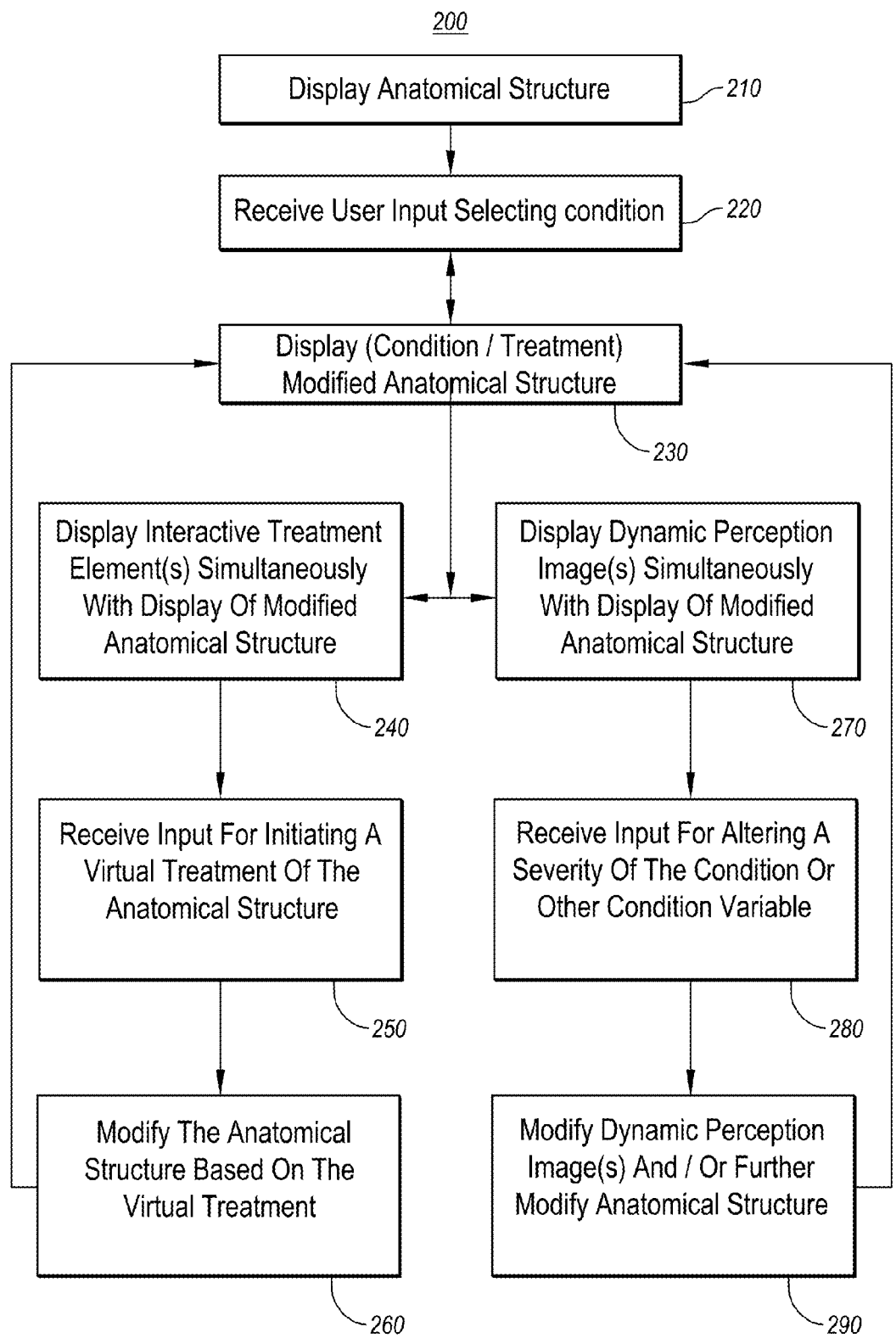
FIG. 2 illustrates a flowchart of acts associated with methods of the invention.

Attention will now be directed to FIG. 2, which illustrates a flow diagram 200 of various acts associated with disclosed methods of the invention and that are associated with facilitating a user's interaction with a representation of an anatomical structure. These acts include, for example, displaying an anatomical structure (210), receiving user input for selecting a condition (220) or treatment related to the anatomical structure, displaying a modified anatomical structure (230) in response to specification of the condition or treatment, displaying interactive treatment elements (240), receiving input for manipulating the modified anatomical structure (250) with selected treatments, and for further modifying the anatomical structure (260). Other illustrated acts include displaying dynamic perception images (270), receiving input for altering a severity of a condition or altering a condition variable (280), and for modifying the perception images with or without further modifying the anatomical structure (290).

These acts of the flow diagram 200 will now be described in greater detail, with specific reference to the interfaces shown in FIGS. 3A-8. Notably, the various acts are described from the perspective of the client system 110. However, correspondingly appropriate acts can also performed by the server 120 and third party systems 140, such as, for example, when the displayed data is obtained from or processed by the server 120 and third party systems 140 prior to being rendered on the client system 110.

The first illustrated act is the act of displaying an anatomical structure 210. This act can include presenting a user with a menu of a plurality of different anatomical structures to select from in response to a user selecting an anatomy tab 312 (FIG. 3A and 3B), for example, from a user interface. This can also include receiving a query from the user, which requests that a particular structure be displayed, in response to typed data entered into an input field of an interface. Alternatively, an anatomical assembly, such as a human body, can be presented to the user and the user can select the portion, subassembly or anatomical element of the body to zoom into and/or to display.

The user input that is used to make the selection of the anatomical structure to be displayed can be provided through touch input entered on a touch screen. Alternatively, the input can be typed input and/or even audible input, such as voice commands. In fact, as described herein, the term "input" and "user input" can comprise any combination of touch input, typed input, voice commands or other types of input entered with any type of input device. In one alternative embodiment, for example, a user provides an image file (e.g., a picture or medical file) as input that is analyzed by the interface and used to identify an anatomical structure that is referenced by or included within the image file and that is subsequently displayed by the interface. In this example, the anatomical structure that is rendered can even include a representation of the user's own body part that is captured in the image and that is reproduced through the interface.

Figure 3A:
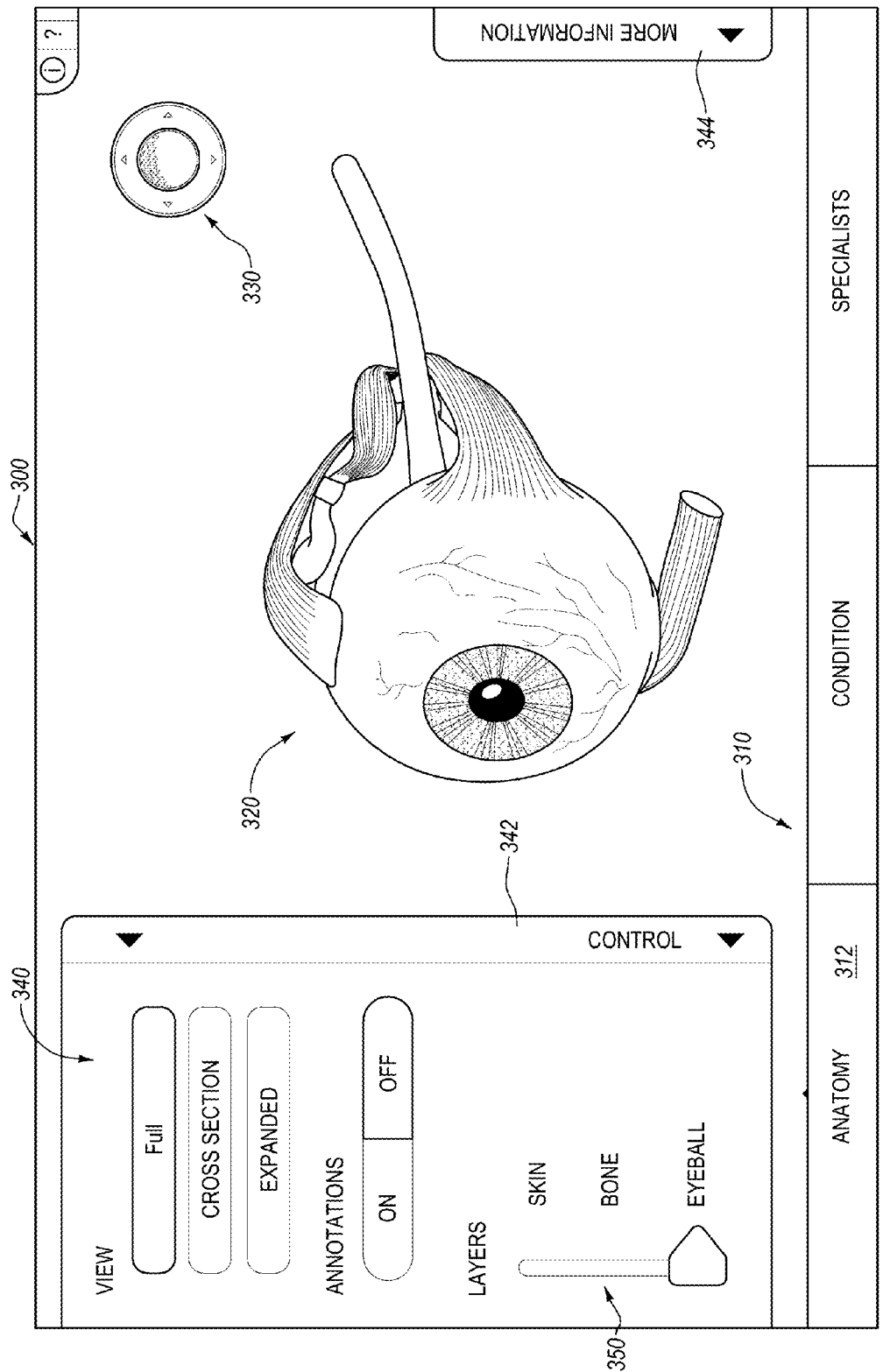
FIGS. 3A and 3B illustrate an exemplary user interface that is configured to illustrate an anatomical structure with user interface elements that can be selected to explore the anatomical structure.

FIG. 3A illustrates one example of an interface 300 that can be used to display an anatomical structure (210). As shown, the presentation of the anatomical structure is made in an interface 300 that also includes a selection bar 310 having different categories of interest, including an anatomy tab 312 that can be selected by a user to initiate the selection and display of the anatomical structure (210). The anatomy tab can also be reflected as an icon, such as icon 391 shown in FIG. 3C.

In the current illustration, the displayed anatomical structure 320 is an eyeball structure. The anatomy of the eyeball can be explored and further displayed (210) through the use of controls and display elements, such as control 330 and controls presented in display menu 340. Control 330 can be manipulated to rotate the displayed anatomical structure 320 about a central point of rotation.

Control 350, shown in display menu 340, can be used to apply or remove different anatomical layers associated with the anatomical structure 320. In the present illustration, the control 350 allows a user to selectively control whether bone and skin layers are to be included with the display of the eyeball structure 320.

Figure 3B:
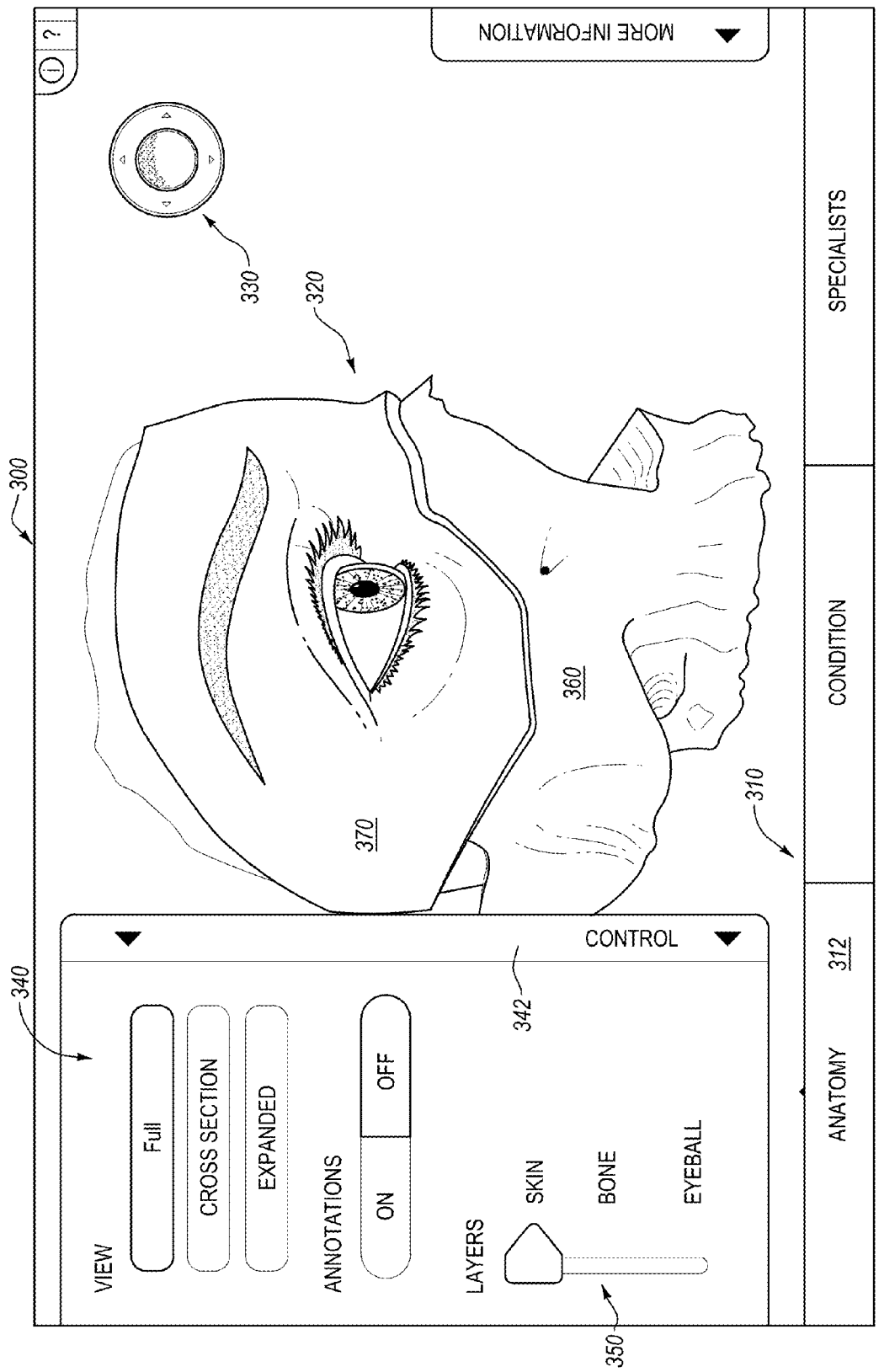

As shown in FIG. 3B, the control 350 is adjusted to display the anatomical structure 320 with corresponding bone 360 and skin 370 layers that are associated with the eyeball structure 320. Although not shown, the control 350 can also be set at the bone setting to cause the anatomical structure 320 to be displayed without the skin 370, but to only include the bone 360 and the eyeball.

It is also possible to configure the control as selection boxes, rather than the slider control 350, to enable a user to selectively check whichever elements they want to be displayed as part of the anatomical structure.

It will be noted that the display menu 340 can be persistently displayed with the anatomical structure 320 or, alternatively, can be hidden and only periodically displayed when a portion of the control display menu 340 is selected from a display tab. For instance a selectable display tab 342 can be presented along a border of the interface 300, such as the more information tab 344 which is presently displayed. When selected, the corresponding control display menu 340 will be displayed.

The more information tab 344, when selected, causes a menu of selectable options to be displayed, such as options for obtaining information related to the displayed anatomical structure 320, conditions and treatments. In some embodiments, the more information tab 344, when selected, presents data associated with a particular medical history or record corresponding to the user and that correlates to the displayed anatomical structure 320. Other types of information, including links to related data, can also be provided, as desired. In some embodiments, the more information tab 344 presents image, video, sound and/or textual data that is contextually relevant to the present view of the anatomical structure 320. While information tab 344 is shown to have a particular configuration, it should be appreciated that other types of information controls can also be used, such as, for example, information icon 394 of FIG. 3C, which is operable, when selected, to access and display additional information and menu options related to the displayed anatomical structures.

As presently shown, the control display menu 340 includes options for selecting a view type to use in rendering the display of the anatomical structure 320, including a full view (currently selected), a cross sectional view, or an expanded view. The expanded view can comprise a more detailed view of the anatomical structure 320 in the form of an exploded view or a view that includes additional anatomical structures. Although not shown, the control display menu 340 can also include other views, such as, but not limited to 3D views (when the client devices are capable of rendering 3D views), inside-out or fly through views, and zoomed views.

In some embodiments, it is useful to provide annotations with the visual representations of the anatomical structures. These annotations can also be selectively turned on or off through the control display menu 340. Currently turned off, the annotations provide identifications, tags and/or notations regarding different elements that are displayed or associated with the rendered anatomical structure 320. The annotations, when turned on, can be persistently displayed with and proximate to any displayed elements included within the display of the anatomical structure 320. Alternatively, the annotations can be hidden and only selectively displayed, even when turned on, in response to a cursor prompt hovering over the element(s) that corresponds to the annotation(s) or in response to user input being received for selecting a corresponding display element. In yet another alternative embodiment, some annotations are only by selectively displayed when a corresponding element is rotated into view. In some embodiments, the annotations also comprise audio and other multimedia content that is accessible through the selection of a link that is presented in the form of an annotation.

Figure 3C:
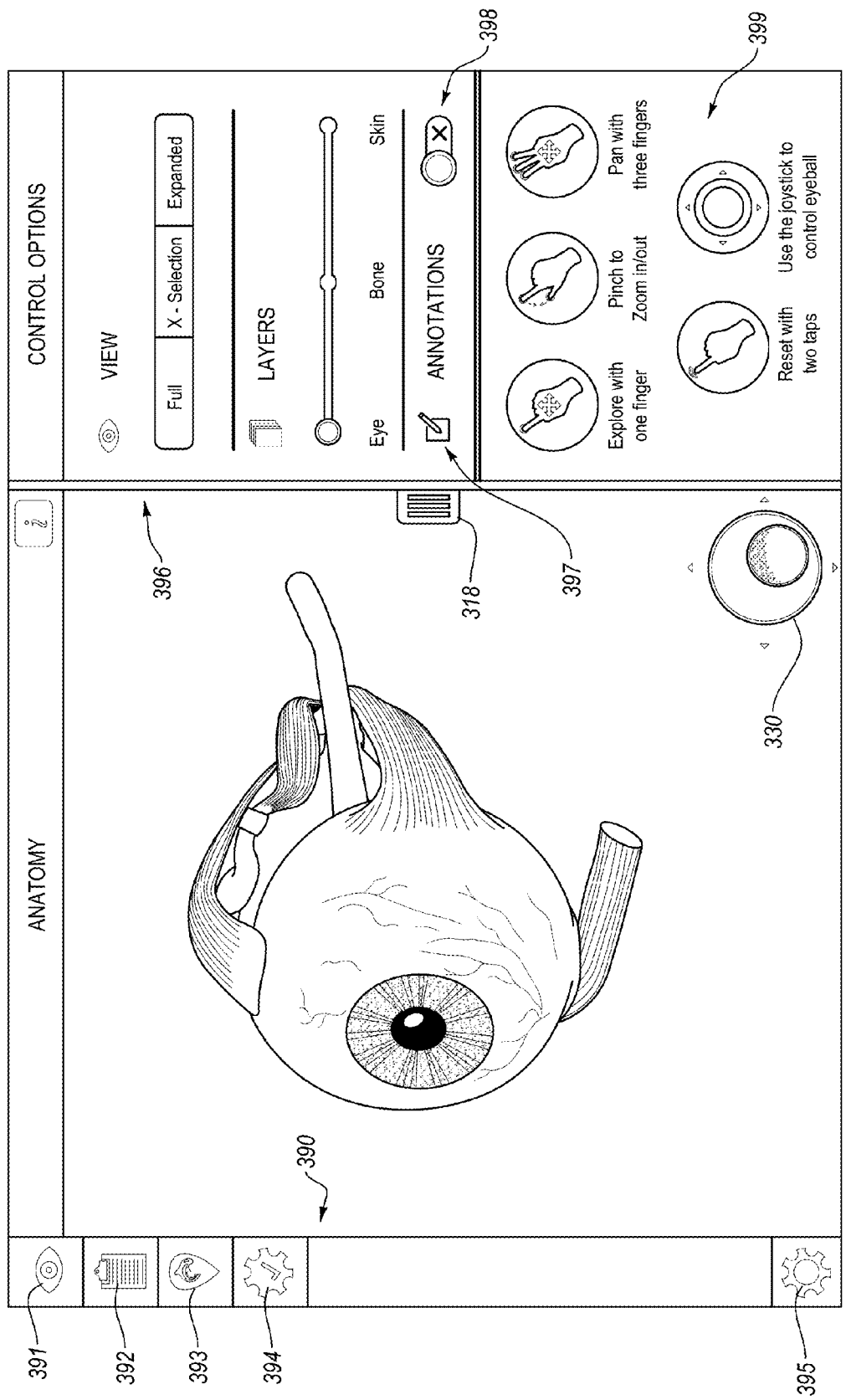
FIG. 3C illustrates another example of a user interface that is configured to illustrate an anatomical structure with user interface elements that can be selected to explore the anatomical structure.

FIG. 3C illustrates another example of a user interface that can be used to display an anatomical structure (210). In this embodiment, however, the selection bar 310 of FIGS. 3A and 3B is reconfigured slightly as selection bar 390, which includes a plurality of icons that are each individually selectable to access corresponding categories of interest. For instance, the selection bar includes icon 391, icon 392, icon 393, icon 394 and icon 395. Icon 391 is operable, when selected, to cause the system to display an anatomical structure that can be explored with user controls, as described above. Icon 392 is operable, when selected, to cause the system to display a condition interface, such as described herein with reference to FIG. 5. Icon 393 is operable, when selected, to cause the system to display a specialist interface, such as described herein with reference to FIG. 8. Icon 394 is operable, when selected, to cause the system to display additional information about a displayed object or feature, such as described herein with reference to information tab 344 of FIG. 3. Icon 395 is operable, when selected, to cause the system to display menu controls for adjusting settings associated with the interfaces or for displaying information about the interfaces.

In FIG. 3C, the displayed eyeball structure can be explored through manipulation of the user control 330, as described above in reference to FIGS. 3A and 3B. Likewise, the anatomy of the eyeball can be further explored and displayed (210) through the use of additional controls and display elements that are accessible through display menu 396. This display menu is similar to the display menu 340 of FIG. 3A and 3B, except that the presentation of the view controls, annotation controls and layer controls are presented slightly differently in the display menu 396 of FIG. 3C.

In one embodiment, the annotations control of the display menu 396 includes a selectable icon 397 that, when selected, enables the medical professional or other user to add annotations. A slide control 398 is also presented with the annotations control for selectably turning the presentation of the annotations on or off It is also noted that the display menu 396 includes a plurality of navigation control instructions 399 which clarify how to navigate the anatomical structure. These control instructions 399 are selectably presented or hidden by expanding or hiding the display menu 396 through user interaction with the selectable display tab 318. In some embodiments, a user can also selectively enable or disable certain navigation controls through interaction with the displayed navigation control instructions/icons 399. For instance, selection of one of the displayed instruction icons 399 can enable/disable the corresponding navigation control, depending on whether it is already enabled or disabled.

The next illustrated act of FIG. 2 includes the receipt of user input selecting a condition (220). The selection of a condition can be made through any type of input, including, but not limited to the selection of the condition tab 412 (FIG. 4A) or a related condition tab icon 392, for example.

In some embodiments, the selection of the condition tab 412 causes a user interface to present a list of different conditions that are relevant to an already identified anatomical structure. In other embodiments, the selection of the condition tab 412 causes a listing of conditions to be presented, which are associated with a particular user, patient, or type of medical practice, as determined by user settings. In yet other embodiments, the selection of the condition tab 412 causes a listing of conditions to be presented that are not specifically limited to a particular user, patient, type of medical practice or anatomical structure but, instead, span a plurality of one or more users, patients, medical practices and/or anatomical structures.

In response to the selection of a condition (220), the invention includes presenting a display of a modified anatomical structure (230). In some embodiments, this includes modifying an already displayed anatomical structure, such as structure 320 in FIGS. 3A and 3B, which is modified and displayed as anatomical structure 420 in FIG. 4A. In other embodiments, this includes making an initial presentation of the anatomical structure in the modified form, without first displaying the anatomical structure in a form absent of the condition-related modifications. In this regard, it will be appreciated that it is not essential for every act of FIG. 2 to be performed or for every act of FIG. 2 to be performed in the exact order that is shown in FIG. 2. Instead, the inventive methods described herein can include any combination and ordering of the described acts. Similarly, the interfaces and systems of the invention can also include any combination of the recited features and aspects described herein.

Figure 4A:
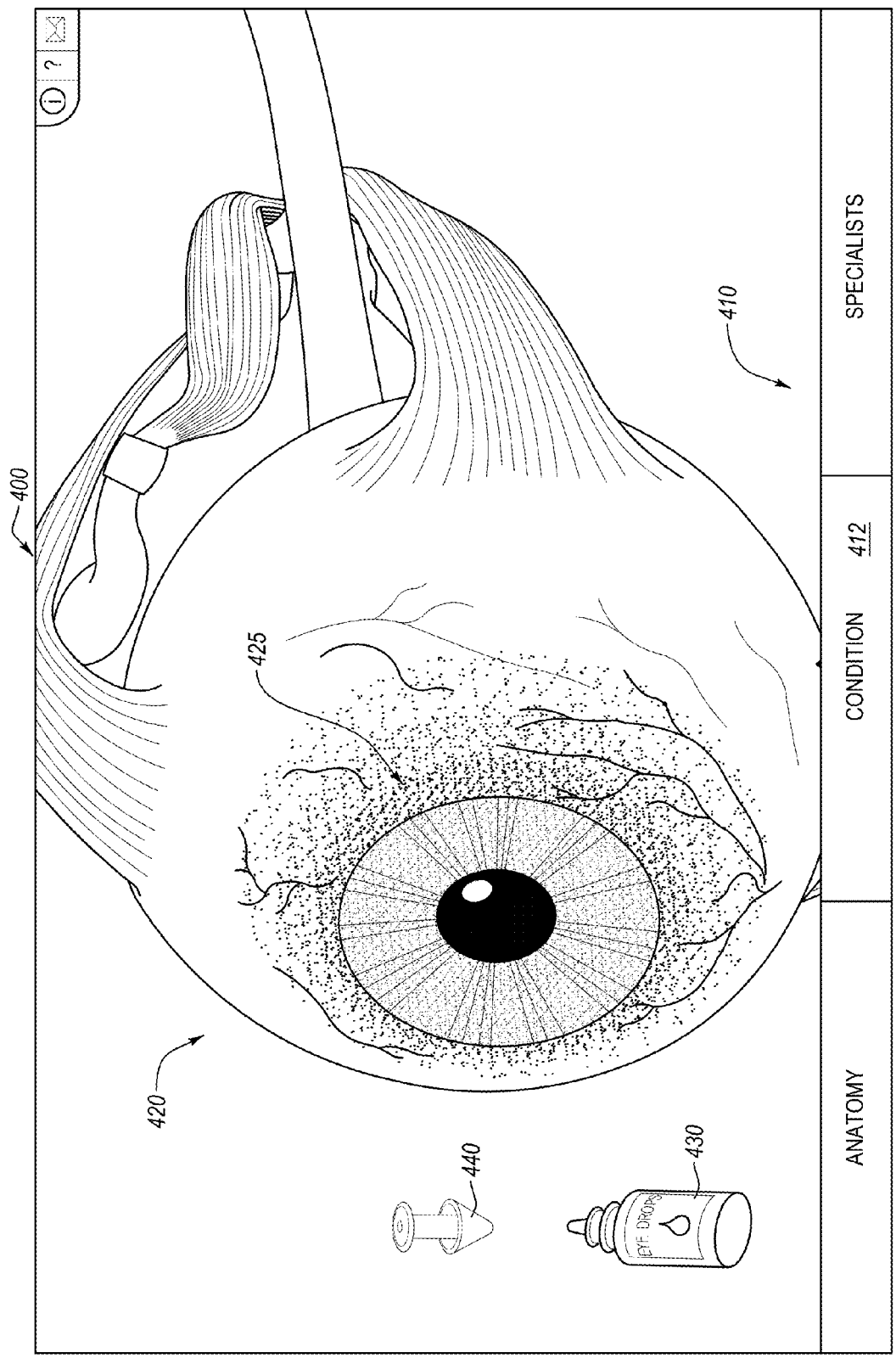
FIGS. 4A-4C illustrate aspects of a user interface that is configured to illustrate an anatomical structure and to modify the anatomical structure in different ways based on selected conditions and treatments.

As shown in FIG. 4A, an interface 400 includes a display of the modified anatomical structure 420, which is rendered with visual display elements 425 associated with the selected condition. In the present illustration, the selected condition is a "dry eye" condition and the display elements 425 reflect agitated tissue resulting from the dry eye condition.

It will be appreciated that any number of conditions can be selected and used to modify the anatomical structure, such that the modification of the anatomical structure may include a collection of modifications associated with a plurality of selected conditions. In some embodiments, the modification of the anatomical structure includes displaying the anatomical structure with additional display elements, which may even be separated from the anatomical structure, such as, but not limited to pain scales associated with pain caused by the condition and viability or longevity scales associated with the viability or other terms related to the condition.

Figure 5:
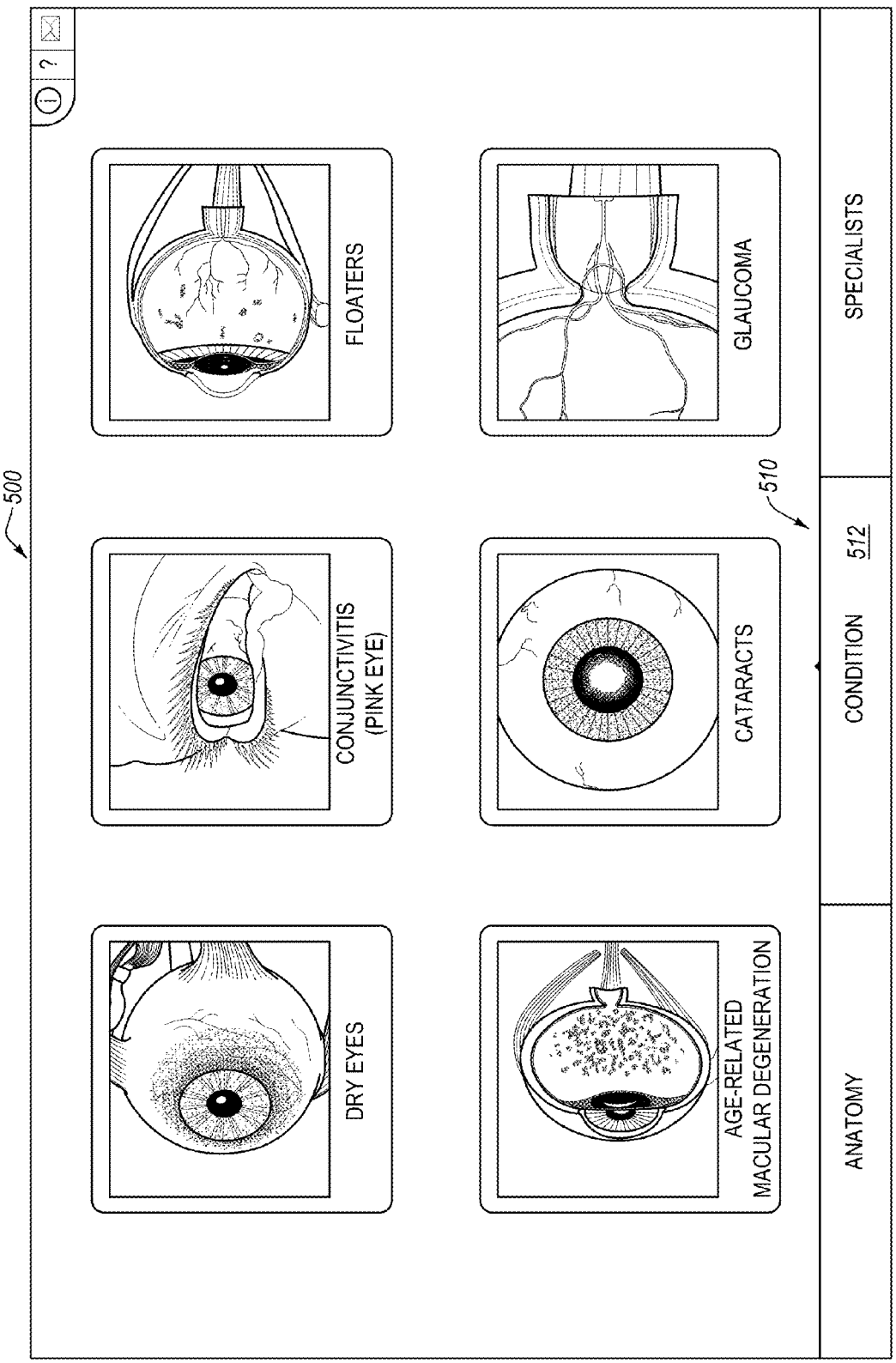
FIG. 5 illustrates an interface display which facilitates the selection of a condition associated with a particular anatomical structure.

Turning now to FIG. 5, an interface 500 is shown that can be used to present a plurality of conditions to a user for selection. The conditions are presented, according to some embodiments, with a visual representation of the condition as well as a textual description or label of the condition. The conditions can include a plurality of different conditions associated with the anatomical structure linked through the anatomy icon 391 or tab 312. In one embodiment, the represented conditions include dry eyes, conjunctivitis, floaters, macular degeneration, cataracts, and glaucoma. Other conditions can also be included or scrolled to by shifting the focus of the screen with touch input. For instance, other conditions like retinal vein occlusion, macular edema, partial blindness and other conditions can be rendered on the screen with their visual representations and textual labels in response to user input detected at the screen or system being used to display the conditions.

In one embodiment, the interface 500 is displayed in response to a user selecting the condition tab 512 from the selection bar 510, in response to selection of another control like condition icon 392, and/or in response to providing a user selection associated with this particular user interface. Although not shown, each of the conditions can be associated with a check box to enable selection of multiple conditions. Alternatively, the user can select multiple conditions simultaneously, such as through multiple simultaneous touch inputs, or through a controlled selection with a keyboard and mouse.

A condition can also be selected in response to user input being directed to one of the illustrated conditions. For instance, the illustrated visual representation and/or the label can comprise an operable link to another interface associated with that condition. Accordingly, a user can select the illustrated label or image to access the interface that is related to the corresponding condition.

Methods of the invention can include displaying data associated with one or more treatments for the selected condition(s) on the user interface(s). For instance, as described in FIG. 2, this can include displaying interactive treatment elements (240), such as the eye drops 430 and punctal plugs 440 shown in FIG. 4A. This interface is only one example of a condition interface that can be accessed through the selection of a condition from the condition interface 500.

By providing information related to treatments for the selected condition(s), a user can be informed as to possible treatments that they were previously unaware of. The user can then select an interactive treatment element to learn more about the treatment options. A specialists tab 820 (FIG. 8) can also be selected to direct a user to a specialist having access to or information about the corresponding treatments and conditions for the anatomical structures.

In one embodiment, the interactive treatment elements (e.g., 430, 440) can be selected and dragged to at least intersect with a displayed portion of the anatomical structure and to initiate a virtual application of the treatment to the anatomical structure that is afflicted with the previously selected condition(s).

Figure 4B:
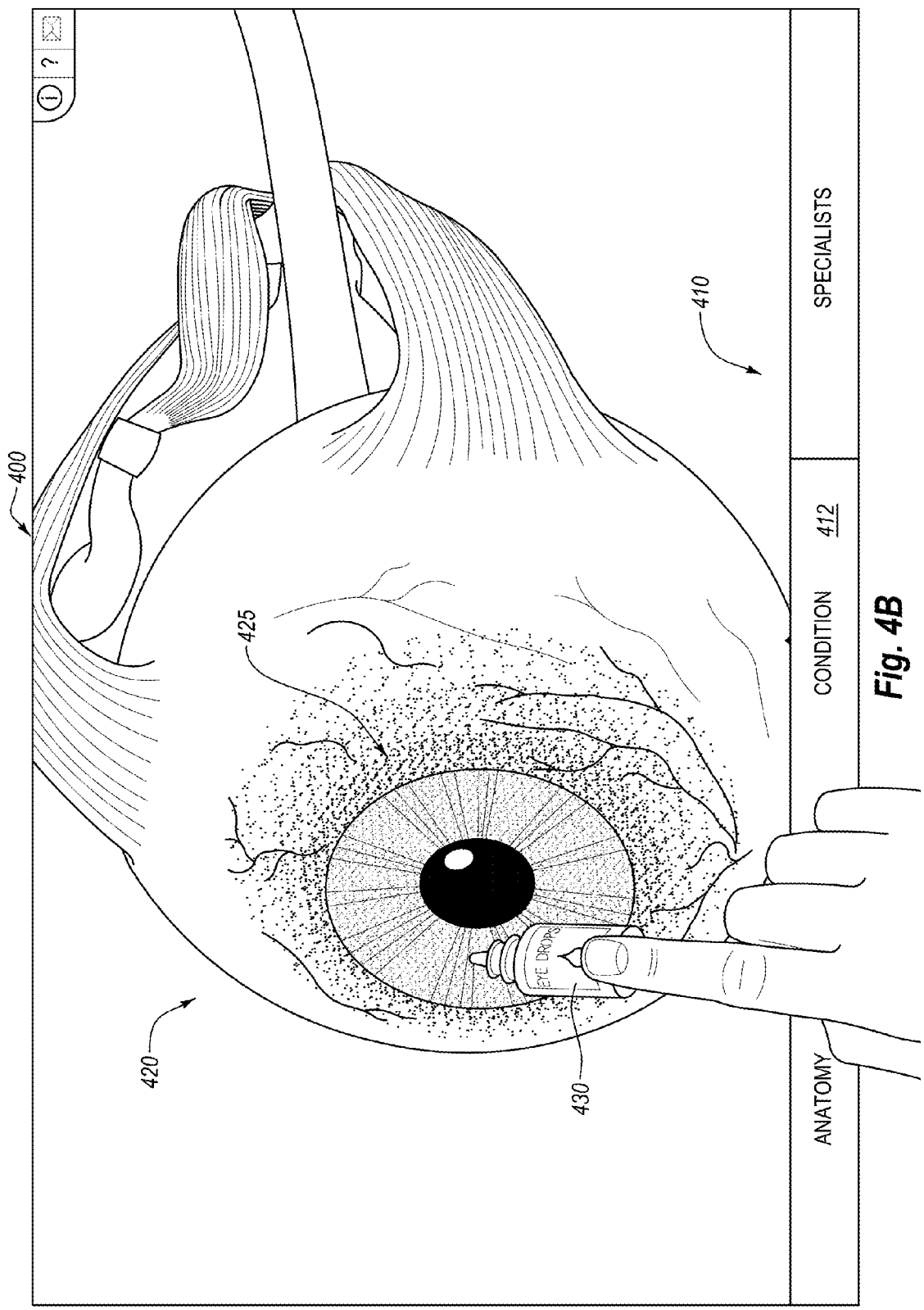

FIG. 4B, for example, illustrates one example in which eye drops 430 have been dragged, via user input, from a first position to a second position that intersects with a displayed portion of the anatomical structure 420 that is afflicted with the dry eye condition. This input initiates a manipulation of the modified anatomical structure and virtual treatment of the dry eye condition. A dynamic representation of the virtual treatments is rendered in the form of streaming video or one or more separate images.

Figure 4C:
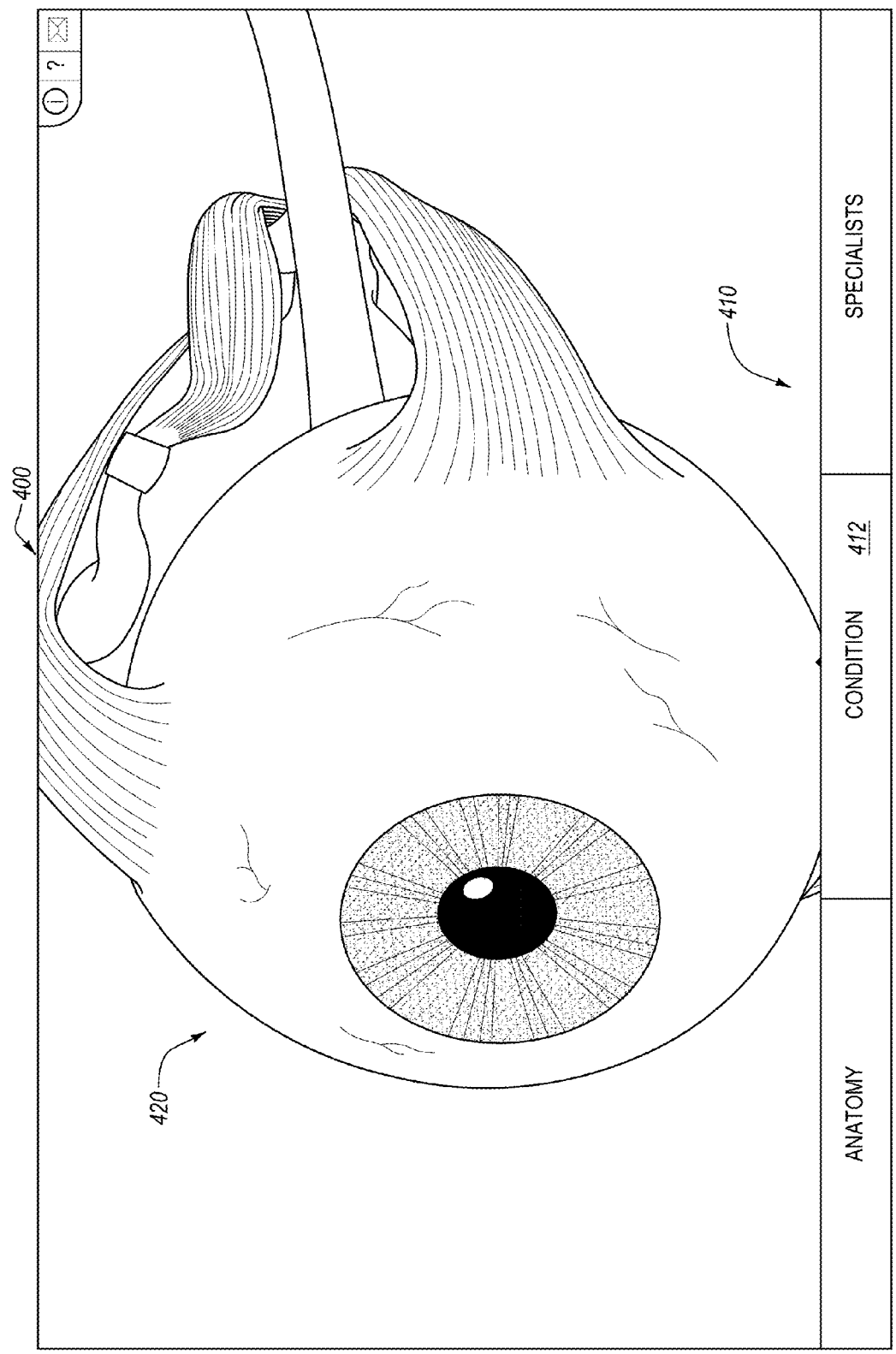

FIG. 4C illustrates one example of an interface representation of the anatomical structure 420 that is displayed after the virtual treatment has been applied (260). Noticeably, the agitated tissue 425 (shown in FIGS. 4A and 4B), which is associated with the dry eye condition, is either reduced or eliminated (FIG. 4C), thereby reflecting the successful treatment of the dry eye condition with the eye drops 430.

In some embodiments, the impact of the virtual treatment associated with a selected and applied treatment may not be visually perceptible. This is particularly true when the treatment element is not applied correctly or when the treatment element is not applied to the appropriate location on the anatomical structure 420. In other embodiments, the visual perception of the virtual treatment only occurs after a predetermined time associated with the treatment. In yet other embodiments, the visual perception of the virtual treatment is only available through supplemental text, video or audio that describes the results of the treatment and without modifying the visual presentation of the anatomical structure 420. One example of this would include presenting a notice regarding a reduction in pain associated with a condition. Alternatively, a pain scale can be displayed as part of the condition and can be modified to reflect the effects of the virtual treatment. Other images, scales or charts can also be modified to reflect the impact of a selected set of one or more treatments on a selected set of one or more conditions on a selected set of one or more anatomical structures.

In some embodiments, the application of treatments is also associated with one or more treatment variable(s), such as a magnitude, duration, sequence or quantity that is requested of the user in response to the selection of the treatments. The treatment variable input provided by the user is used to specify a particular duration for applying the treatment, a dosage to apply, a frequency for repeating treatment, a sequence for applying treatment(s), and/or any other relevant treatment information. The receipt of the treatment variable input is included within the act of receiving input for initiating the virtual treatment (250).

Other embodiments of the invention also include displaying dynamic perception images associated with the selected condition(s). These images reflect, for example, the relative perception that an individual afflicted with the selected condition(s) might experience.

Figure 6A:
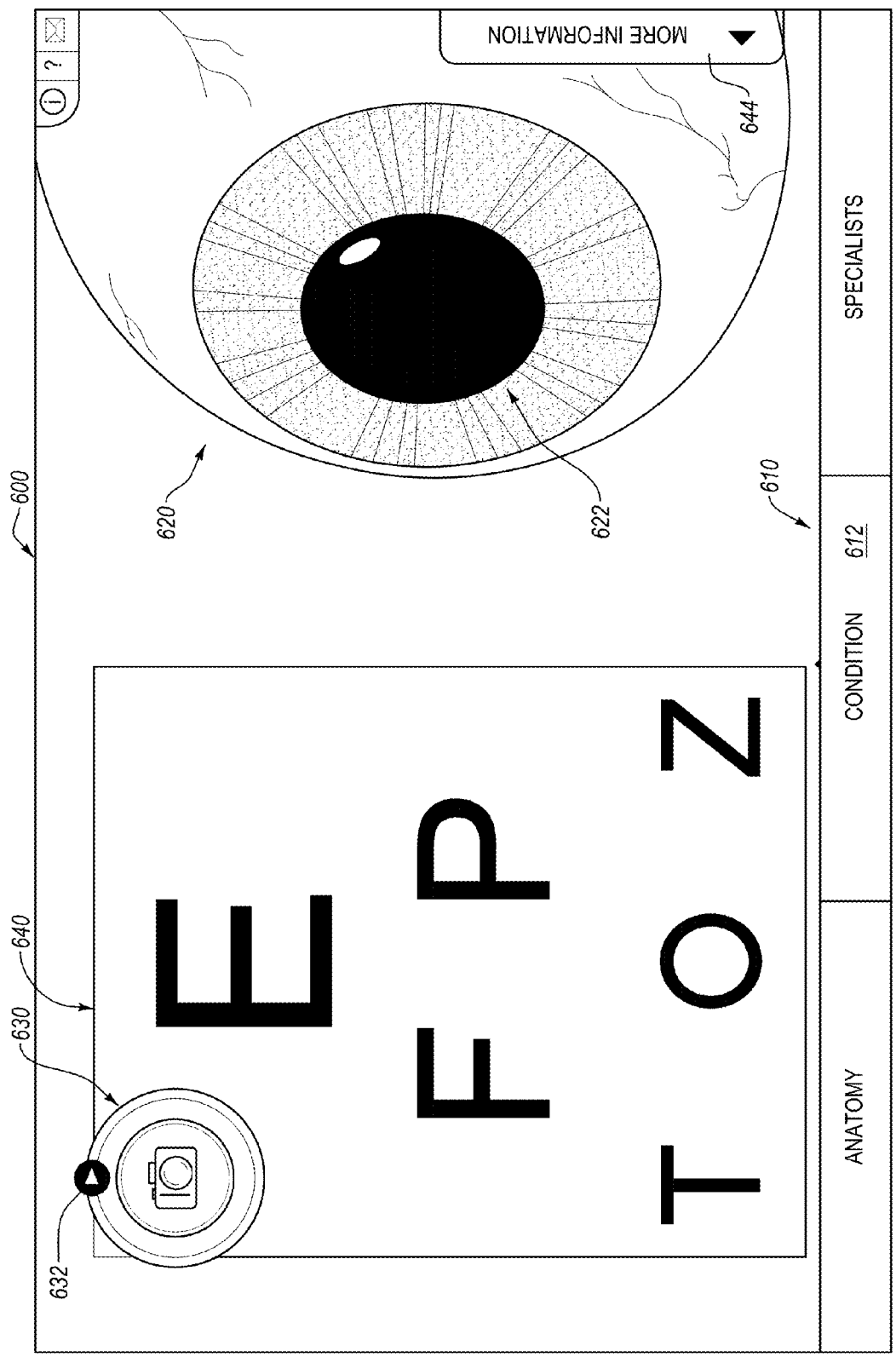
FIGS. 6A and 6B illustrate aspects of a user interface that is configured to illustrate an anatomical structure with a corresponding perception image along with a condition severity control that can be manipulated through user input to modify the anatomical structure and/or perception image based on a correspondingly selected severity of the condition.
Figure 6B:
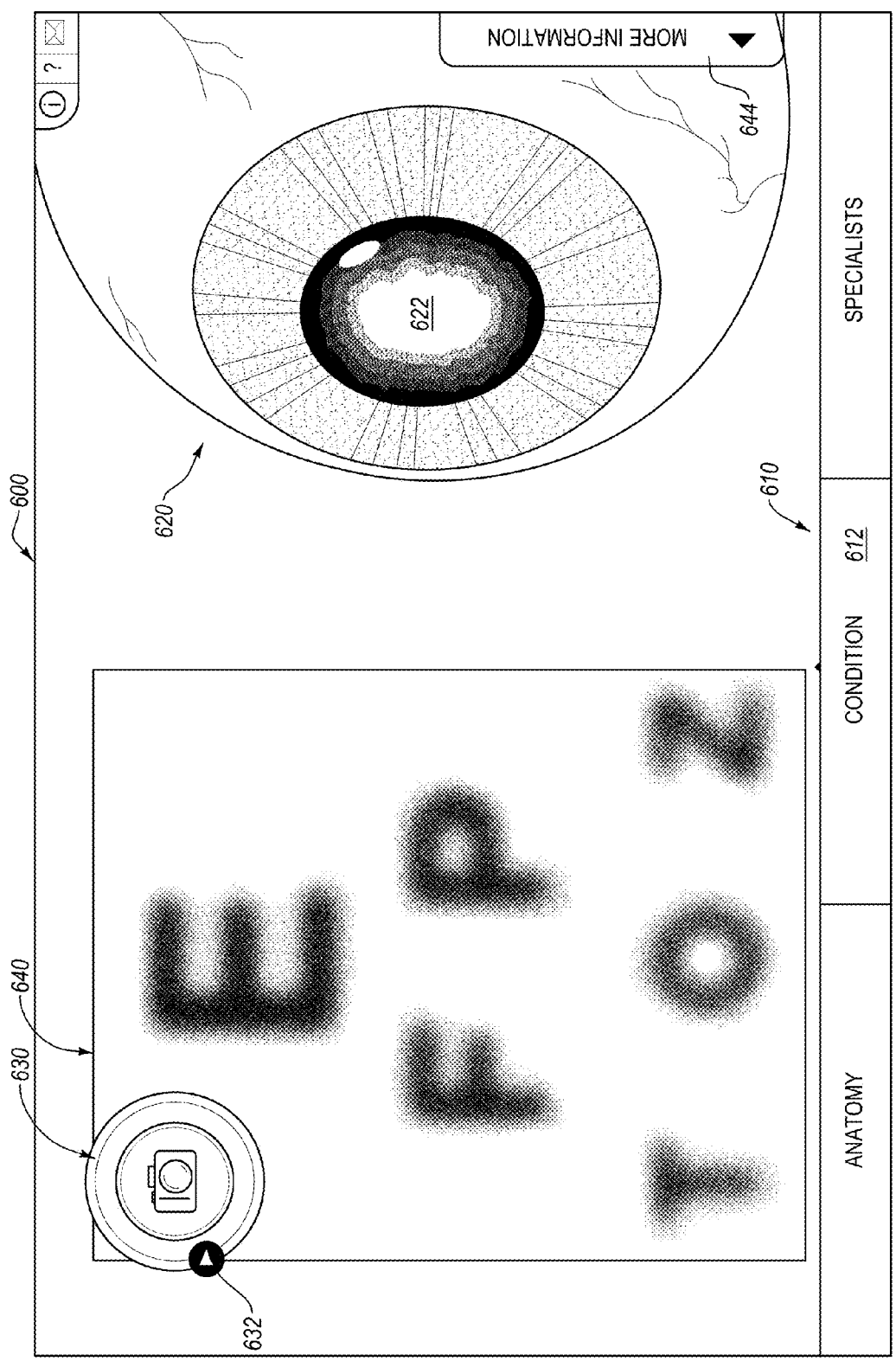

FIGS. 6A and 6B illustrate an interface 600 in which an anatomical eye structure 620 is displayed along with a perception image (270) comprising a representation of a vision chart 640. The interface 600 also includes a selection bar 610 and corresponding condition tab 612 that have previously been discussed and through which this interface 600 can be accessed. In particular, the interface 600 can be presented in direct response to a user selecting the condition tab 612 and selecting a corresponding condition that is presented to the user, such as through interface 500 or another interface. The more information tab 644 can also be used to provide access links to the interface 600 and/or to enable the display of the perception image 640 and/or a condition control 630.

As suggested earlier, the perception image 640 represents a relative view of an image that a user experiencing a selected condition might see. In the present example, the selected condition is cataracts. This condition was previously selected through one of the previously described interface elements.

As shown in FIG. 6A, the condition control 630 has a control feature 632 that is presently set at the top of the control 630, in such a manner as to reflect that the cataract condition is at a beginning stage, having a nominal effect or no effect on the anatomical eye structure. Correspondingly, the perception image 640 also has no alteration or nominal alteration to reflect a correspondingly relative view that a person having the cataract condition might experience when the condition is at the beginning stage or has a minimal severity. The control feature 632 of the severity control can be moved through user input selecting and dragging the feature 632, or with other input, to dynamically alter the corresponding severity of the selected condition.

FIG. 6B, for example, illustrates an embodiment in which the anatomical structure is modified in response to the input that specifies or alters the severity of the selected condition (280). In particular, as shown, the lens portion 622 of the anatomical eye structure 620 has been affected by the cataract condition. The perception image has also been dynamically modified (290) to reflect the relative perception of the image that a user afflicted with the cataract would see when the cataract condition is advanced to the severity setting that is currently established by the relative position of the control feature 632. Noticeably, the contrast and visual perception of the image 640 in FIG. 6B is diminished from the representation of the image 640 in FIG. 6A. These changes to the anatomical eye structure and the perception image can occur smoothly and dynamically in response to user input (280), including touch input that moves the control feature 632 around the control 630. For instance, these changes can occur as video-type animations. Alternatively, the changes can occur in a limited number of stages, even as few as two stages, including a beginning stage shown in FIG. 6A and a final stage shown in FIG. 6B, with the transition between stages occurring immediately in response to a user removing their finger from the touch pad surface, after moving the control feature 632.

Data that is used by the interface to control the diminished visual properties of the dynamic perception image and the modification of the anatomical eye structure is accessible through the network connections 130 described in reference to FIG. 1 and can be stored in any of the systems 110, 120, 140. This data correlates the designated impact of a condition and/or treatment of the condition on the corresponding anatomical structures. Accordingly, as a user designates the impact (severity) of the condition and/or treatment through the interface controls, the corresponding impact data is retrieved and used to make the necessary modifications and representations on the interfaces of the invention.

In some embodiments, in which multiple conditions have been selected, it is possible to present multiple independent controls for each of the corresponding conditions.

In some embodiments, the controls also include scales or other indicators (not shown) to provide a percentage, age or other quantification associated with the severity of the selected condition(s) as controlled by the relative position of the corresponding control feature(s). In yet other embodiments, the control 630 comprises a linear and sliding scale control feature, rather than the radial dial reflected in the Figures, to quantify the severity of the selected condition(s). In some embodiments, an input field can also be provided to receive input that specifies a relative severity of the condition(s).

Figure 7A:
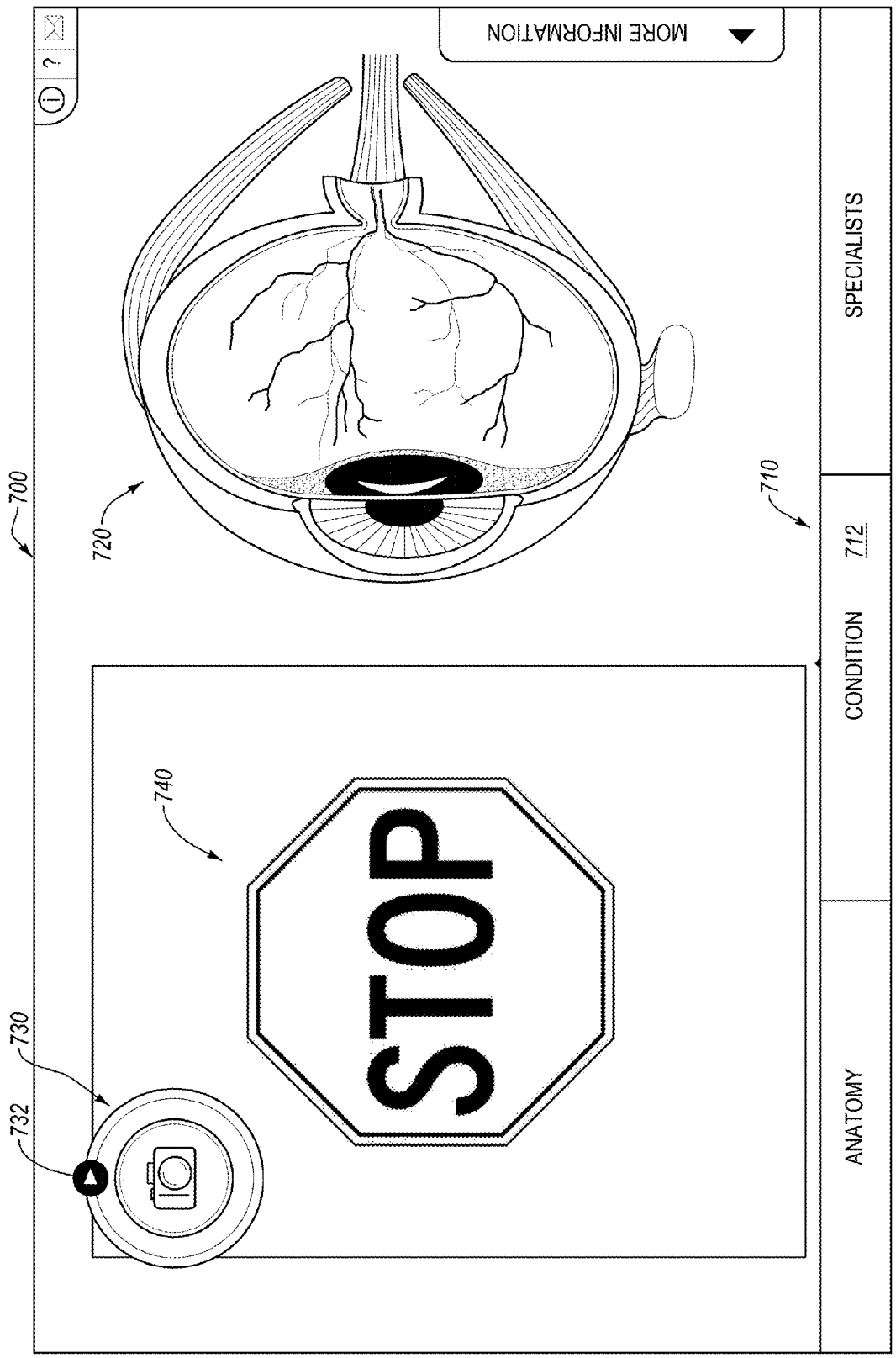
FIGS. 7A and 7B illustrate aspects of a user interface that is configured to illustrate an anatomical structure, a corresponding perception image, and a condition severity control that can be manipulated through user input to modify the anatomical structure and/or perception image based on a correspondingly selected severity of the condition.
Figure 7B:
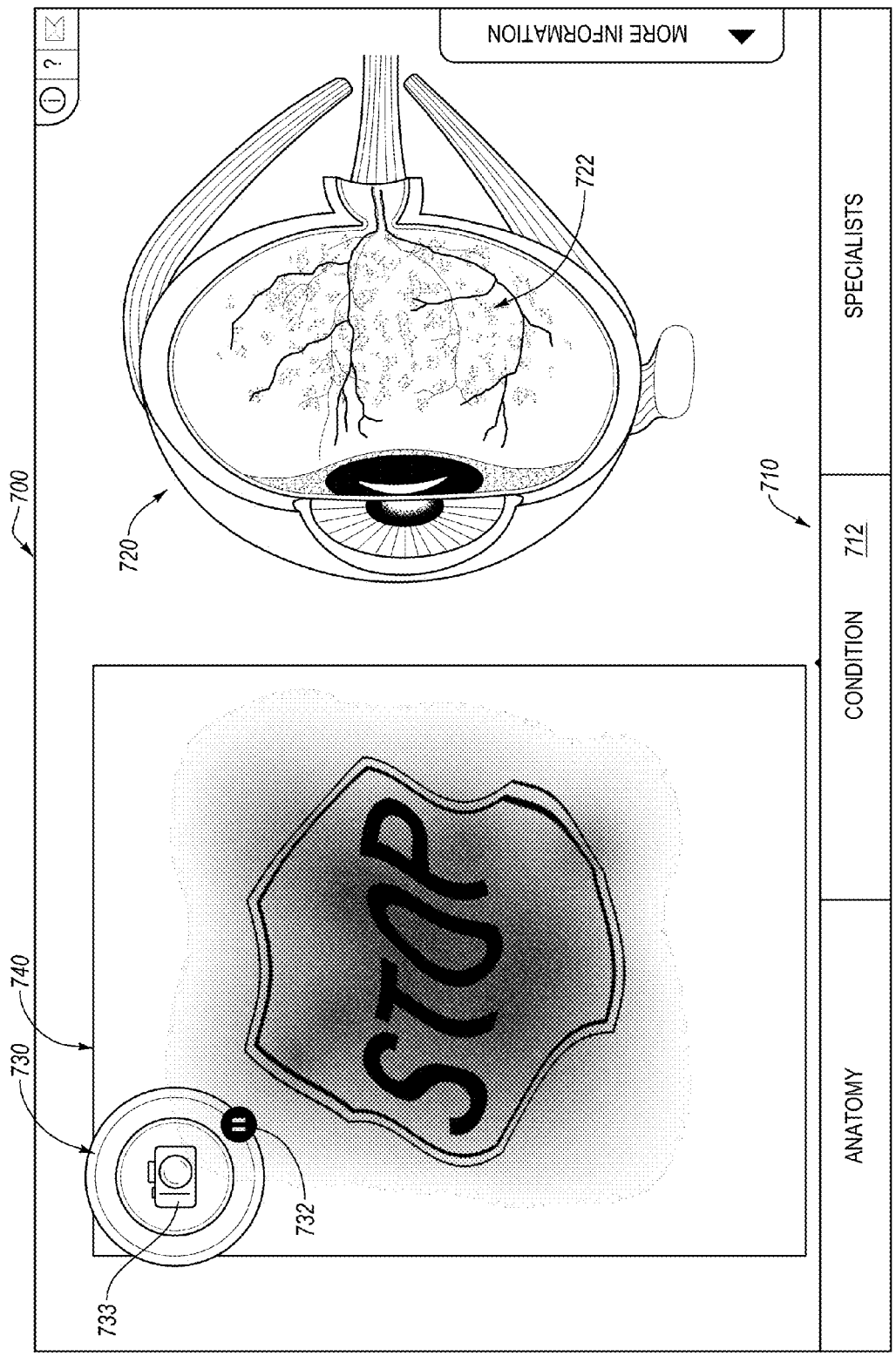

FIGS. 7A and 7B illustrate another example of an interface 700 that has been configured to illustrate an anatomical structure 720, such as an eye, that has been afflicted with a selected condition, such as macular degeneration. This interface is another non-limiting example of an interface that can be accessed through selection of one of the conditions that are illustrated in the condition interface of FIG. 5, for example.

The interface 700 is also configured, in the present embodiment, to simultaneously display a dynamic perception image 740, which currently includes a representation of a stop sign. In one embodiment, this image is a static image that is either a stock image or an image photograph taken by the camera of the device.

The interface also includes a severity control 730 having a control feature 732 that can be selectively moved or modified to dynamically adjust the severity of the selected condition (e.g., macular degeneration and/or another selected condition). As indicated above, this interface 700 can be accessed through user input, such as touch input entered at selection bar 710 and condition tab 712 or through any of the other interface elements previously discussed.

As also discussed above, the manipulation of the control feature 732, from a first position shown in FIG. 7A to the adjusted position shown in FIG. 7B, dynamically controls the corresponding modification to the anatomical structure shown in the Figures, as well as the modification to the perception image 740. In particular, the increased severity in the condition (as specified by the adjustment to the control feature 732 about the control 730) causes macular degeneration effects 722 to be displayed on the anatomical eye structure, as well as to diminish the relative visual perception of the image 740. These changes can be smoothly made in a dynamic real-time manner, on-the-fly, as the control feature 732 is manipulated. This dynamic real-time modification is particularly beneficial when the image is a streaming video image that is captured in real-time. In other embodiments, correspondingly similar treatment controls can also be presented to dynamically adjust the application of a treatment according to a time scale, intensity scale, dosage scale, or any other relevant scale and to correspondingly modify the display of the anatomical structure and the perception image in response to the virtual treatment of the condition, as specified by the manipulation of the treatment controls. The treatment controls (not shown) can be used independently or in conjunction with the condition severity controls described above.

FIG. 7B also illustrates a camera control icon 733 that is presented within the control 730 and that is operable, when selected, to activate camera functionality of the device or system being used to render an image that is displayed on the interface 700. This is shown and described in more detail below in reference to FIG. 7C.

Figure 7C:
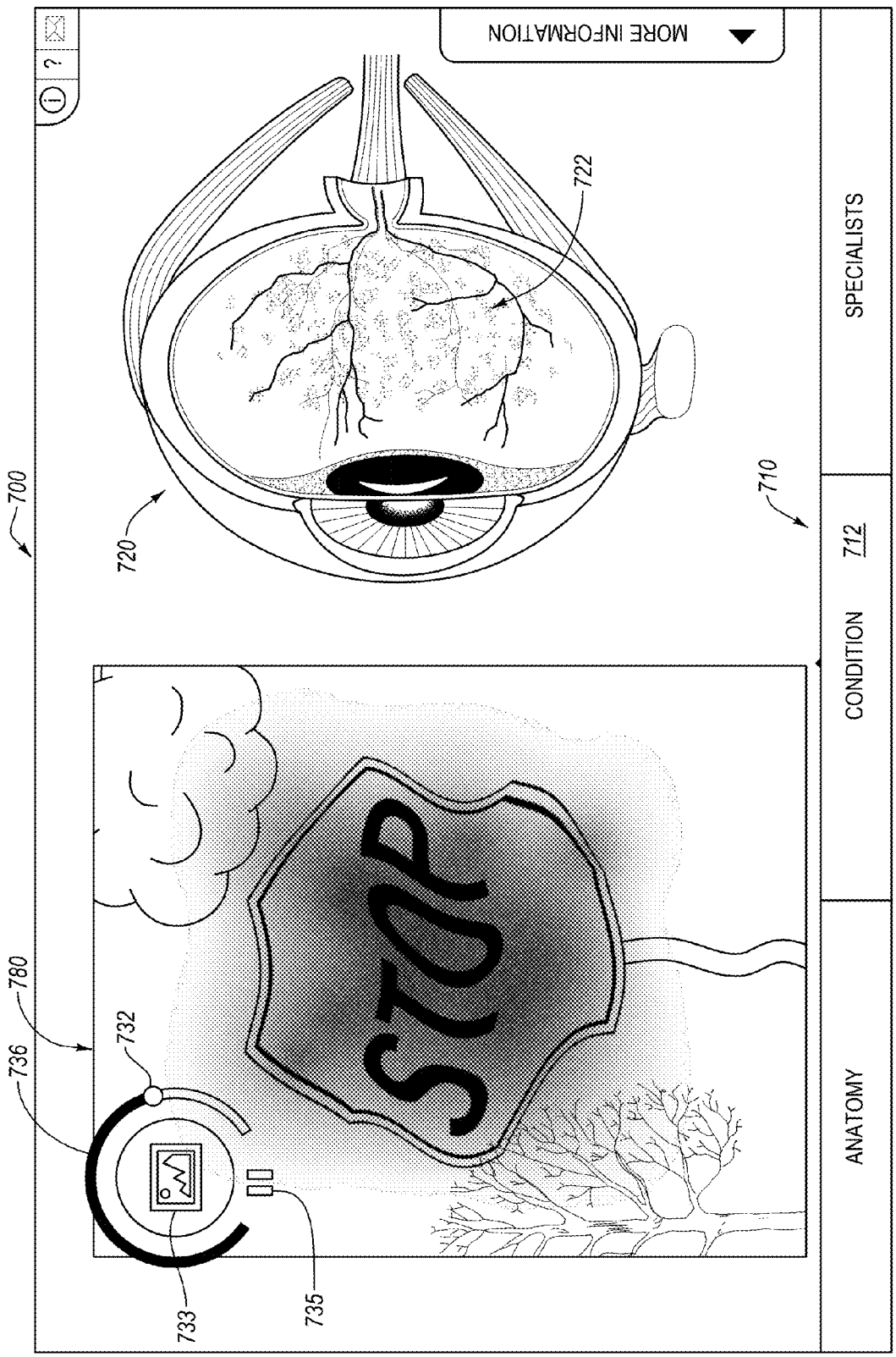
FIG. 7C illustrates another user interface that is configured to illustrate an anatomical eye structure and a perception image that is rendered as a streaming video and that is dynamically modified to reflect an impact of a condition on the eye structure.
Figure 8:
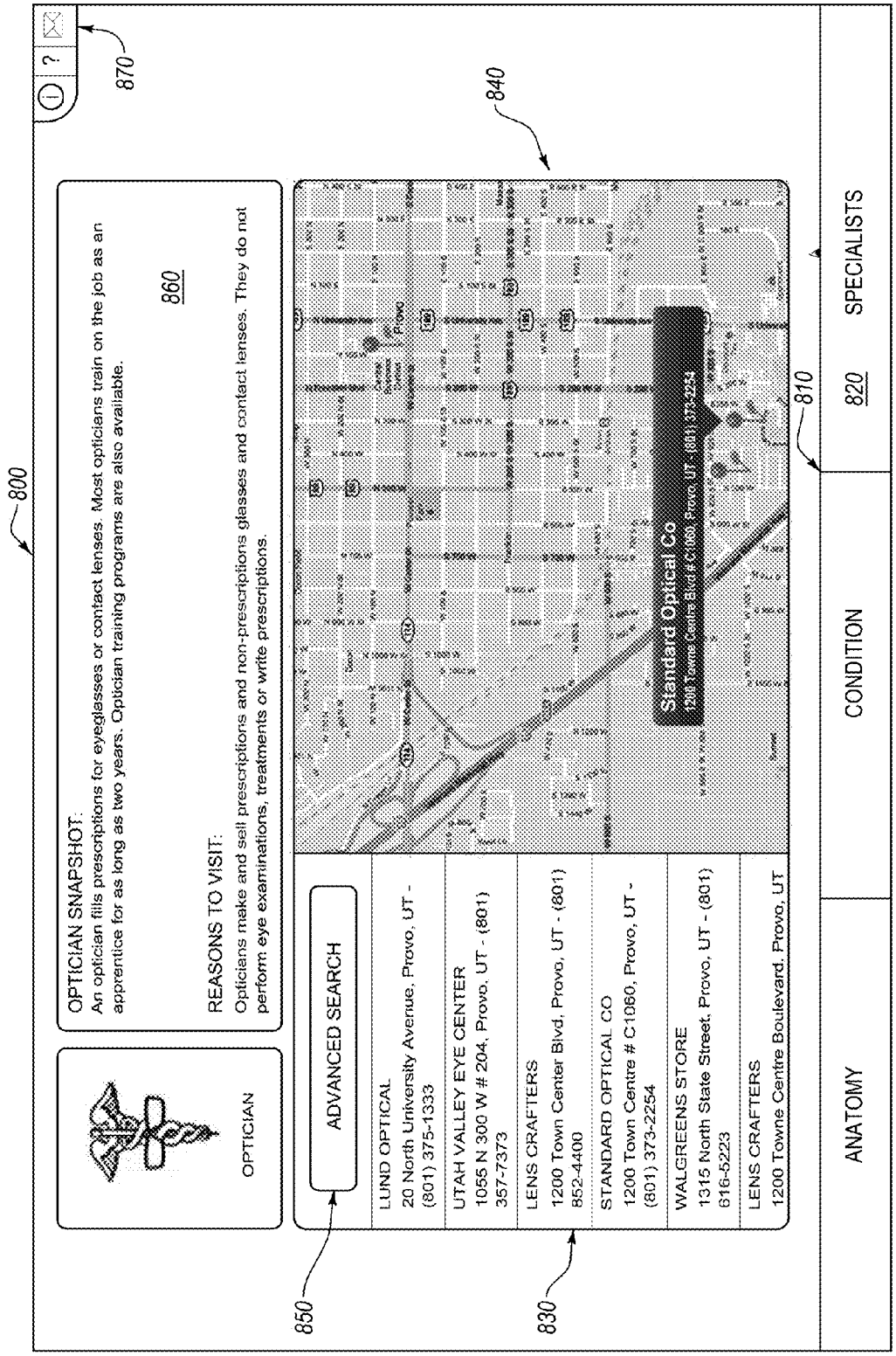
FIG. 8 illustrates one example of a user interface display that can be displayed when a user selects a specialist interface element, and which includes contact information and other information associated with one or more specialists.

FIG. 7C illustrates an example of an interface that can be accessed through one or more of the links or objects described above and which can be used to further help educate a user about the impact of a degenerative or vision impaired condition.

As shown, the interface 700 includes the anatomical representation of an eye as well as an image 780 that is reflecting a real-time image that is a streaming image that is continuously captured by the camera in real-time. In alternative embodiments, the image 780 is a static image that was taken as a photograph by the device camera in response to a user selection of the camera control 733 or another button or control associated with the camera or device.

As presently illustrated, the image 780 shown in FIG. 3C includes a stop sign and an outdoor scene that is being captured in real-time in response to the camera control 733 having been selected from FIG. 7A or 7B and in response to the camera being pointed at the stop sign, for example.

Once the camera control 733 is selected, it is changed to reflect a static image icon (e.g., FIG. 7C) in place of the camera icon that was previously reflected in FIG. 7B. This change helps indicate that an additional selection of the camera control 733 will switch the interface back to a static shot of an image (e.g., image 740 for example), rather than the continuous stream of video images 780 that are currently being captured and displayed by the camera in real-time.

One benefit of enabling a continuous stream of video images 780 to be captured in real-time is that a user can move the device camera around and get new images that are automatically displayed and modified with the selected condition at the selected severity, to further reflect how the condition would affect the user. This is possible, because the user can easily compare the modified image 780 on the screen with their own real perception of the scenery/objects that they can see with their own eyes and without the use of the device. This can be particularly helpful when the user is selectively moving the camera between objects in the distance and close proximity.

The control 730 can also include a progression meter 736 that reflects how far the condition has progressed or a level of severity of the condition, such as, for example, when the meter control 732 progresses around the meter 736. The meter 736 can also be filled or otherwise shaded or colored to reflect the progression of the condition.

In one embodiment, the meter control 732 is moved dynamically in response to user input dragging the meter control 732. As the meter control 732 is moved, the severity of the condition is also adjusted and used to modify the image 780 and the anatomical object accordingly, as indicated above, to reflect the impact of the condition at the currently set severity.

In alternative embodiments, the meter control 732 is moved automatically in response to a user pushing a play button. The user can also pause the meter control 732, by pressing a pause button, so that progression of the condition can be paused at a particular severity. In some embodiments, the play button and the pause button are the same button which changes its configuration in response to being selected, from a play state to a paused state. This play/pause button can be positioned directly on the meter control, as shown in FIGS. 7A and 7B, or alternatively, can be positioned at a different location as shown in FIG. 7C (e.g., button 735). As presently reflected, the pause/play button 735 is in a play state, with a visual appearance of a pause indicator. This indicates that the condition is continuing to progress and the meter control 732 is dynamically moving around the progression meter 736, but that this progression will be paused once the pause/play button 735 is selected. Accordingly, once the pause/play button 735 is pressed, the progression of the meter control 732 will pause, as will the changes to the anatomical object and further degradation of the image 780. The visual appearance of the pause/play button will also change to reflect a play indicator, which can be selected to resume the progression of the condition and corresponding movement of the meter control 732.

In view of the foregoing, it will be appreciated that the image 780 is dynamically changed in response to movement of the camera as well as in response to progression of the condition, wherein the progression of the condition is reflected by the movement of the meter control 732 or another visual indicator of the condition severity.

While the foregoing embodiments have been described with respect to anatomical optic structures, such as eyeballs, it will be appreciated that the invention also extends to the application of the related interfaces to other anatomical structures. By way of example, and not limitation, an arm or other appendage can be rendered with conditions related to muscular tension, arthritis, ligament tearing, broken bones, and so forth. The appendage can then be displayed with any number of corresponding anatomical layers and can be displayed with corresponding treatments. The virtual application of the treatments can be rendered with the anatomical structures to help illustrate the effects of the treatments for certain conditions on the anatomical structure(s). In these embodiments, an appendage animation can replace the perception image to reflect the corresponding movement, strength or other attribute of the selected appendage as the relative severity of the condition or the application of a treatment is adjusted through one or more controls.

Specialists associated with the various conditions and treatments can also be identified through the interfaces of the invention. According to one embodiment, the server system 120 and third party systems 140 continuously update a repository of specialists and corresponding contact information. This repository is included in the recordable-type storage 180*b* described above and can also be stored on the client systems 110 at recordable-type storage 180*a*.

Various interface links, such as specialist link 820 (FIG. 8) can be accessed from the selection bar 810 or other interface objects, such as specialist icon 393. Once selected, an interface, such as interface 800 can be presented to the user. This interface 800 can include various contact information for the specialists associated with a selected condition or anatomical object. Location information associated with the specialists' offices can also be pinpointed on a map 840 and/or can be provided in list form 830. In some embodiments, an advanced search option 850 can be selected to provide a rich query option to filter the search results based on qualifications, specialties, location, tenure, insurance affiliations, referrals, and/or any other filter. Other information can also be provided in other display frames 860. Contact interface elements, configured to launch communications with the specialists, such as email, telephony, instant messaging, and so forth can also be provided in other interface objects 870.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for using an interactive computer interface to dynamically reflect how one or more user-selectable conditions and severity of those conditions can affect a user's vision, the method comprising:
   receiving user input at a computing device that identifies a condition that can affect vision;
   using a camera associated with the computing device to capture a plurality of images that are streaming video images captured in real-time by the camera associated with the computing device;
   displaying the plurality of images as they are captured by the computing device, without modification, such that the plurality of images are displayed in a manner that reflects how the plurality of images would generally appear to a user when vision of the user is not yet affected by the identified condition;
   displaying an interface control that is operable to receive user input for modifying a severity of the condition;
   receiving user input at the interface control that selects a severity of the condition; and
   in response to selection of the severity, dynamically modifying the plurality of images as they are being captured in real-time by the camera associated with the computing device, to display an altered version of the plurality of images that reflects an impact of the condition at the selected severity, the altered version of the plurality of images being displayed in such a manner as to reflect how the plurality of images would appear to the user if the user's vision was affected by the condition at the selected severity.

2. The method of claim 1, wherein the method further includes:
   receiving user input that identifies a new selected severity of the condition; and
   modifying the plurality of images and dynamically displaying the plurality of images according to the new selected severity and in such a manner as to reflect how the plurality of images would appear to the user when the user's vision is affected by the condition at the new selected severity.

3. The method of claim 1, wherein the selected severity is based on an age of the condition.

4. The method of claim 1, wherein the interface control is displayed simultaneously with the plurality of images.

5. The method of claim 1, wherein the method further includes displaying a user-selectable link that is selectable to access additional information about the condition and which is displayed with the plurality of images and the user control.

6. The method of claim 1, wherein the method further includes displaying a representation of an eye simultaneously with the plurality of images and the interface control.

7. The method of claim 6, wherein the representation of the eye is also dynamically changed as the plurality of images is modified to reflect an impact of the condition on the eye.

8. A computing system comprising:
   at least one processor; and
   memory having stored computer-executable instructions which, when executed, implement a method for using an interactive computer interface to dynamically reflect how one or more user-selectable conditions and severity of those conditions can affect a user's vision, wherein the method includes:
      receiving user input at the computing system that identifies a condition that can affect vision;
      using a camera associated with the computing system to capture a plurality of images that are streaming video images captured in real-time by the camera associated with the computing device;
      displaying the plurality of images as they are captured by the computing system on a display screen of the computing system, without modification, such that the plurality of images are displayed in a manner that reflects how the one or plurality of images would generally appear to a user when vision of the user is not yet affected by the identified condition;
      displaying an interface control that is operable to receive user input for modifying a severity of the condition;
      receiving user input at the interface control that selects a severity of the condition; and
      in response to selection of the severity, dynamically modifying the plurality of images as they are being captured in real-time by the camera associated with the computing device, to display an altered version of the plurality of images that reflects an impact of the condition at the selected severity, the altered version of the plurality of images being displayed in such a manner as to reflect how the plurality of images would appear to the user if the user's vision was affected by the condition at the selected severity.

9. The computing system of claim 8, wherein the interface control is displayed simultaneously with the plurality of images.

10. The computing system of claim 8, wherein the method further includes displaying a specialist link that is operable, when selected, to display information about one or more specialist associated with the condition.

11. A computer program product comprising one or more recordable-type storage device having stored computer-executable instructions which, when executed by at least one computing processor, implement a method for using an interactive computer interface to dynamically reflect how one or more user-selectable conditions and severity of those conditions can affect a user's vision, wherein the method includes:
    receiving user input at a computing device that identifies a condition that can affect vision;
    using a camera associated with the computing device to capture a plurality of images that are streaming video images captured in real-time by the camera associated with the computing device;
    displaying the plurality of images as they are captured by the computing device, without modification, such that the plurality of images are displayed in a manner that reflects how the plurality of images would generally appear to a user when vision of the user is not yet affected by the identified condition;
    displaying an interface control that is operable to receive user input for modifying a severity of the condition;
    receiving user input at the interface control that selects a severity of the condition; and
    in response to selection of the severity, dynamically modifying the plurality of images as they are being captured in real-time by the camera associated with the computing device, to display an altered version of the plurality of images that reflects an impact of the condition at the selected severity, the altered version of the plurality of images being displayed in such a manner as to reflect how the plurality of images would appear to the user if the user's vision was affected by the condition at the selected severity.

12. The computer program product of claim 11, wherein the selected severity is based on an intensity of the condition.

13. The computer program product of claim 11, wherein the interface control provides a user selectable option for initiating a continuous play and progression of the condition.

14. The computer program product of claim 11, wherein the condition is a condition selected from a displayed plurality of conditions that are each displayed simultaneously within a condition interface that displays a visual representation of said each condition along with a textual label of each corresponding condition.

* * * * *